United States Patent
Jacques (10) Patent No.: US 9,675,727 B2
(45) Date of Patent: Jun. 13, 2017

(54) METHOD AND DEVICE FOR TREATING BURSITIS

(75) Inventor: Danniel Jacques, Bexley (AU)

(73) Assignee: MEDIWISE PTY LTD., Bexley, New South Wales (AU)

(*) Notice: Subject to any disclaimer, the term of this patent is extended or adjusted under 35 U.S.C. 154(b) by 939 days.

(21) Appl. No.: 11/932,933

(22) Filed: Oct. 31, 2007

(65) Prior Publication Data

US 2008/0254107 A1    Oct. 16, 2008

(30) Foreign Application Priority Data

Apr. 10, 2007   (AU) .................................. 2007901915

(51) Int. Cl.
| | | |
|---|---|---|
| A61K 9/70 | (2006.01) | |
| A61K 31/785 | (2006.01) | |
| A61K 31/78 | (2006.01) | |
| A61K 31/715 | (2006.01) | |
| A61P 19/02 | (2006.01) | |
| A61L 15/16 | (2006.01) | |
| A61L 15/00 | (2006.01) | |

(52) U.S. Cl.
CPC ............. *A61L 15/16* (2013.01); *A61K 9/7023* (2013.01); *A61K 31/715* (2013.01); *A61K 31/78* (2013.01); *A61L 15/00* (2013.01); *A61K 31/785* (2013.01)

(58) Field of Classification Search
None
See application file for complete search history.

(56) References Cited

U.S. PATENT DOCUMENTS

| | | | |
|---|---|---|---|
| 5,431,622 A | 7/1995 | Pyrozyk et al. | |
| 5,447,531 A | 9/1995 | Wood | |
| 5,869,533 A * | 2/1999 | Holt | 514/627 |
| 5,952,367 A | 9/1999 | Pak | |
| 6,087,382 A | 7/2000 | Bonner, Jr. et al. | |
| 6,102,937 A | 8/2000 | Cramer et al. | |
| 6,123,717 A * | 9/2000 | Davis et al. | 607/109 |
| 6,187,031 B1 | 2/2001 | Douglas | |
| 6,560,483 B1 | 5/2003 | Kumar et al. | |
| 6,660,901 B2 | 12/2003 | Church | |

(Continued)

FOREIGN PATENT DOCUMENTS

| | | | |
|---|---|---|---|
| CN | 1239203 C | * | 2/2006 |
| EP | 1 005 844 A1 | | 6/2000 |
| WO | WO 2005/009488 A2 | | 2/2005 |

OTHER PUBLICATIONS

Kiliç I. et al. (2003) Eur. J. Dermatol. 13; 503-504.*

(Continued)

*Primary Examiner* — Bethany Barham
*Assistant Examiner* — Dominic Lazaro
(74) *Attorney, Agent, or Firm* — Knobbe, Martens Olson & Bear, LLP (57) ABSTRACT

The invention relates to a method for treating a subject for a bursitis. The method comprises applying to the skin surface covering a body part or region affected by the bursitis a composition capable of transdermally attracting fluids from the body part or region or its proximity, wherein the composition includes at least one adsorptive or absorptive agent, and leaving the composition in contact with the skin for sufficient time to allow the composition to transdermally absorb or adsorb at least a portion of the body fluids from the body part or region.

13 Claims, 2 Drawing Sheets

(56) References Cited

U.S. PATENT DOCUMENTS

| | | | |
|---|---|---|---|
| 6,660,902 B2 | 12/2003 | Widlund et al. | |
| 6,660,903 B1 | 12/2003 | Chen et al. | |
| 6,765,000 B2 | 7/2004 | Bonner, Jr. et al. | |
| 6,812,254 B1 | 11/2004 | Barr et al. | |
| 2003/0047027 A1* | 3/2003 | Sato | 75/228 |
| 2004/0042965 A1* | 3/2004 | Usui et al. | 424/40 |
| 2005/0171199 A1* | 8/2005 | Murrell | 514/509 |
| 2006/0110415 A1* | 5/2006 | Gupta | 424/401 |
| 2006/0134187 A1* | 6/2006 | Victor | 424/449 |
| 2006/0142712 A1* | 6/2006 | Quincy | 604/364 |

OTHER PUBLICATIONS

Safe Solutions website accessed Nov. 25, 2009 at http://www.safesolutionsinc.com/detox_foot_pads.htm.*

Danniel's Bursitis Treatment website accessed Nov. 25, 2009 at http://treatment-bursitis.com/.*

Magee, J. L., et al., Elementary Processes in Radiation Chemistry. II. Negative Ion Formation by Electron Capture in Neutral Molecules, J. Am. Chem. Soc., 1951,73 (2), pp. 523-532.*

English Language Translation of CN 1239203 C.*

Vaillant, L., et al., Skin acceptance of transcutaneous nitroglycerin patches: a prospective study of 33 patients, Contact Dermatitis, 23 (1990), pp. 142-145.*

Asada, T. et al. 2002 "Science of Bamboo Charcoal: Study on Carbonizing Temperature of Bamboo Charcoal and Removal Capability of Harmful Gases" *Journal of Health Science* 48(6): 473-479.

Kaymak-Ertekin, F. et al. 2000 "Modelling of mass transfer during osmotic dehydration of apples" *Journal of Food Engineering* 46: 243-250.

Lu, S. et al. 2007 "Effective removal of zinc ions from aqueous solutions using crab carapace biosorbent" *Journal of Hazardous Materials* 149: 208-217.

Nomanbhay, S.M. et al. 2005 "Removal of heavy metal from industrial wastewater using chitosan coated oil palm shell charcoal" *Electronic Journal of Biotechnology* 8 (1): 43-53.

Rosenholm, J.B. et al. 2008 "Materials cohesion and interaction forces" *Adv Colloid Interface Sci* 141:48-65.

Whitehouse, A.G.R. et al. 1932 "The Osmotic Passage of Water and Gases through the Human Skin" *Proceedings of the Royal Society of Lond. Series B, Containg Papers of a Biological Character* 111(773):412-429.

Yucha, C. and Keen, M. 1996 "Renal regulation of extracellular fluid volume and osmolality" *ANNA Journal* 23:487-495.

Berne, R.M. et al. 2004 in *Physiology 5th Ed.* Mosby, St. Louis, MO, p. 439.

Cardone, D.A. et al. 2002 "Diagnostic and Therapeutic Injection of the Elbow Region" *American Family Physician* 66(11):2097-2100.

Cardone, D.A. et al. 2003 "Diagnostic and Therapeutic Injection of the Hip and Knee" *American Family Physician* 67(10):2147-2152.

Inoué, S. et al. 1989 "Biological activities caused by far-infrared radiation" *Int J Biometerol* 33: 145-150.

Jéquier, E. et al. 2010 "Water as an essential nutrient: the physiological basis of hydration" *European Journal of Clinical Nutrition* 64:115-123.

Keyes, J.L. 1999 in *Fluid, Electrolyte, and Acid-Base Regulation*, Jones and Barlett Publishers, Inc. New York, NY, pp. 31-38.

Liang, J. et al. 2010 "Microstructure and Far Infrared Emission Properties of Tourmaline Powders Eroded by Hydrochloric Acid" *J Nanoscience and Nanotechnology* 10:2077-2082.

Lin, C-C. et al. 2008 "Far Infrared Therapy Inhibits Vascular Endothelial Inflammation via the Induction of Heme Oxygenase-1" *Arteriosclerosis, Thrombosis, and Vascular Biology* 28:739-745.

Macintyre, B.A. et al. 1968 "Mechanism of enhancement of eccrine sweating by localized heating" *Journal of Applied Physiology* 25(3):255-260.

Meng, J. et al. 2010 "Effects of particle Size on Far Infrared Emission Properties of Tourmaline Superfine Powders" *Nanoscience and Nanotechnology* 10:2083-2087.

Newburgh, L.H. et al. 1942 "The Insensible Loss of Water" *Physiological Reviews* 22(1):1-18.

Quayle, J.B. et al. 1976 "An Operation for Chronic Prepatellar Bursitis" *The Journal of Bone and Joint Surgery* 58-B(4):504-506.

Reeve, E.B. et al.1960 "Blood Volume Regulation" *Annu Rev Physiol* 22:349-380.

Ritz, P. et al. 2005 "The Importance of Good Hydration for Day-to-Day Health" *Nutrition* Reviews 63(6):S6-S13.

Sawka, M.N. et al. 2005 "Human Water Needs" *Nutrition Reviews* 63(6):S30-S39.

Shibasaki, M. et al. 2006 "Neural control and mechanisms of eccrine sweating during heat stress and exercise" *J Appl Physiol* 100:1692-1701.

Sokoloff, L. 1978 in *The Joints and Synovial Fluid* vol. 1, Academic Press, NY, pp. 132-135.

Stirling, M.H. et al. 2000 "A model of human water balance" *Journal of Thermal Biology* 25:187-190.

Szabó, G. 1962 "The Number of Eccrine Sweat Glands in Human Skin" in *Biology of Skin vol. III, Eccrine sweat glands and eccrine sweating*, pp. 1-5.

Yu, S-Y et al. 2006 "Biological effect of far-infrared therapy on increasing skin microcirculation in rats" *Photodermatology Photoimmunology & Photomedicine* 22:78-86.

http://www.detoxi.co.uk/research.htm. Detoxi—Detox *The Power to Detox in a Patch*; (2004). Detoxi Ltd. UK.

http://footsies.com.au/footsies/; (2005) Thinklife Pty. Ltd. WA Australia.

http://www.takarapatch.com/; (2004) Aurora Designs LLC, Burlington, MA, USA.

http://www.buylifewaveplus.com/; (2006) LifeWave Inc., CA, USA.

http://www.au.shopping.com/xGS-pain%20patch~NS~1~linkin_id-8023164; (1997) eBay Inc., CA, USA.

http://www.healerpatch.com/bursitis.html; (2002) OneRom Group Inc, NY, USA.

http://www.anaesthesiaMCQ.com; (2004)'Fluid Physiology—3.2 Insensible Water Loss' by Kerry Brandis, Victoria, Australia.

Detoxion Ionic Detox Patch [retrieved on Oct. 22, 2013] Retrieved from the Internet at web.archive.org/web/20060207174619/http://holistec.com/Detoxion.htm; published on Feb. 7, 2006, as per Wayback Engine.

Amethyst Bio-Mat, on the World-Wide-Web at: alternativesolutions.net/biomatpro.htm; Site available online since at least Sep. 9, 2004 (Sep. 9, 2004): on the internet at web.archive.org/web/20040909194743/http://www.alternativesolutions.net/biomatpro.htm.

The Amethyst Bio Mat, on the World-Wide-Web at: cc-healingarts.com/upload/bio_mat_info.pdf. published after Sep. 9, 2004.

* cited by examiner

METHOD AND DEVICE FOR TREATING BURSITIS

RELATED APPLICATIONS

This application claims the benefit of Australian Provisional Application No. 2007901915 filed Apr. 10, 2007.

FIELD OF THE INVENTION

The present invention relates to methods for treating bursitis and other inflamed and swollen conditions, including abscesses, boils, blisters and cysts, as well as to compositions for said methods.

DESCRIPTION OF THE RELATED ART

Bursae are fluid-filled sacs located throughout the body at locations where surfaces move relative to one another, for example at or near joints and at points where muscles and tendons glide over bones. The function of a bursa is to decrease friction between two surfaces that move in different directions.

Bursitis is the inflammation of a bursa. Normally, the bursa provides a slippery surface that has almost no friction. When a bursa becomes inflamed, it loses its gliding capabilities, and becomes increasingly irritated when it is moved. The condition may be acute or chronic.

Bursitis usually results from a repetitive movement or due to prolonged and excessive pressure. Patients who rest on their elbows for long periods or those who bend their elbows frequently and repetitively (for example, a custodian using a vacuum for hours at a time) can develop elbow bursitis, also called olecranon bursitis. Similarly in other parts of the body, repetitive use or frequent pressure can irritate a bursa and cause inflammation such as may occur in shoulder bursitis, trochanteric (hip) bursitis and prepatellar (kneecap) bursitis. Other areas that may be affected include the Achilles tendon and the foot and wrist.

Another cause of bursitis is a traumatic injury. Following trauma, such as a car accident or fall, a patient may develop bursitis. Usually a contusion causes swelling within the bursa. The bursa, which had functioned normally up until that point, now begins to develop inflammation, and bursitis results. Once the bursa is inflamed, normal movements and activities can become painful.

Bursitis may also be caused by rheumatoid arthritis, gout, or infection. Sometimes the cause cannot be determined. Bursitis commonly occurs in the shoulder, knee, elbow, and hip. Chronic inflammation can occur with repeated injuries or attacks of bursitis.

The excess fluids that accumulate within the bursa sac during bursitis may spontaneously begin to reabsorb and, hence, the bursitis will heal naturally. Unfortunately, due to the very fact that bursitis occurs near joints, the inflamed bursa often undergoes repeated agitation so that the bursitis becomes persistent and does not heal.

When this occurs, or if bursitis causes pain and discomfort, medical intervention is normally recommended.

Current methods for treating bursitis can be moderately to extremely invasive and have the risk of leading to further complications. Additionally, the costs involved with the current treatments create an increased financial burden on the heath system.

NSAIDs: non-steroidal anti-inflammatory drugs (NSAIDs), including aspirin, ibuprofen (Advil, Motrin, others) and naproxen sodium (Aleve, Naprosyn), can help relieve pain. But if taken immediately after an injury, they may actually increase swelling. What's more, NSAIDs can have side effects, especially if you take them for long periods or in amounts greater than the recommended dosage. Even small doses may cause nausea, stomach pain, stomach bleeding or ulcers; and large doses can lead to kidney problems and fluid retention.

NSAIDs also have a ceiling effect, which means there's a limit to how much pain they can control. If you have moderate to severe pain, exceeding the dosage limit probably won't relieve your symptoms. Taking two different NSAIDs at the same time also won't provide more relief and may increase your risk of side effects.

Physical Therapy: normally, the goal of physical therapy is to strengthen the muscles around an injury. Whilst physical therapy is non-invasive, it is generally used for rehabilitation rather then for active bursitis. Physical theory requires a case by case assessment and may be limited in use for the disabled or elderly. It can be costly and may require visits to an athletic club, fitness center or clinic. Generally treatment times require several weeks.

Aspiration: removal of the fluid within the bursa sac by aspiration/needle is invasive and often painful. It creates the risk for infection and rupture of a tendon or muscle damage located in the path of the injection. Additionally, on many occasions the patent needs repeated treatment as fluid returns.

Corticosteroid injections: injections of a corticosteroid drug into the affected area may help reduce the symptoms and provide pain relief. Usually the patent must wait at least four months between injections. The injections aren't effective in all cases and cause some of the same side effects that oral steroid medications do, including an increased risk of infection, water retention and elevated blood sugar levels. Additionally the patent has the risk of allergic reactions.

Another possible complication is "post-injection flare"—joint swelling and pain several hours after the corticosteroid injection—which occurs in approximately one out of 50 patients. It is not known if joint damage may be related to frequent corticosteroid injections. Generally, repeated and numerous injections into the same joint/site should be discouraged. Other complications, though infrequent, include depigmentation (a whitening of the skin), local fat atrophy (thinning of the skin) at the injection site and rupture of a tendon or muscle damage located in the path of the injection.

Surgery: as with all major surgical procedures, complications can occur. Some of the most common complications following surgery for trochanteric bursitis include     anesthesia complications
    thrombophlebitis (DVT)
    infection
    nerve or blood vessel injury
    failure of the operation Additionally, the cost of surgery creates a large financial burden on the heath system.

Bursitis caused by infection is generally treated with antibiotics. Sometimes the infected bursa must be drained surgically.

Bursitis due to underlying conditions such as arthritis and gout are more difficult to treat and recur more frequently. The best management in these situations is to avoid flare-ups of gouty attacks or arthritic episodes, and to avoid activities which cause bursitis.

In summary, the consensus for bursitis treatment involves one or more of the following:

1. resting and immobilising the affected area, applying ice to reduce swelling and taking non-steroidal anti-inflammatory drugs (NSAIDs) to relieve pain and reduce inflammation;
2. sometimes, doctors may recommend physical therapy or exercises to strengthen the muscles in the area;
3. aspiration of the fluid if it does not naturally re-absorb or if the patent is experiencing pain;
4. injection of corticosteroid drug into the bursa to relieve inflammation (must not do if there is infection);
5. if the bursitis is caused by an infection, antibiotics will be needed; and
6. sometimes the bursa needs to be surgically drained, or removed.

These remedies suffer from one or more of the following disadvantages:
i) unreliable efficacy;
ii) side-effects (especially NSAIDs) and complications;
iii) invasiveness;
iv) long term treatment; and
v) expense.

Other conditions resulting in accumulation of excess body fluids in body parts or regions include stenosing tenosynovitis (trigger finger) and DeQuervain's Syndrome.

Trigger finger, or trigger thumb, is a type of stenosing tenosynovitis in which the sheath around a tendon in a thumb or finger becomes swollen or a nodule forms on the tendon itself. In either case, the tendon can no longer slide freely through its sheath. Affected digits may become painful to straighten once bent, and may make a soft crackling sound when moved. More than one finger may be affected at a time, while it usually affects the thumb or middle or ring finger.

Typical treatments include non-steroidal anti-inflammatory drugs, hand splinting, corticosteroid injections directly around the tendon and sheath, or surgical release of the sheath.

DeQuervain's syndrome (also known as washerwoman's sprain, Radial styloid tenosynovitis or De Quervain's disease), is an inflammation of the sheath or tunnel, similar to tenosynovitis that surrounds two tendons that control movement of the thumb. It may be caused by the repetitive motion of the thumb constantly being required to move up and down (usually associated with using a computer keyboard or typewriter or guitar playing with ulnar deviation) and can be included in a loose group of conditions called repetitive strain injuries.

Symptoms are pain and swelling over the thumb side of the wrist, possibly numbness on the back of the thumb, and difficulty gripping.

Management of DeQuervain's disease involves (1) discontinuing or modifying the precipitating motions and (2) reducing the inflammation. Given the irritability of the tendons, short term splinting of the thumb via a thumb spica is often required to prevent re-aggravation with activities of daily living. Frequent and localized icing for short periods of time throughout the day have as an archaic treatment been used, and will reduce the inflammation. There is no peer reviewed objective evidence to support that any electromodality such as ultrasound or other passive treatment (acupuncture) will accelerate treatment. By far the most effective method of treatment is the injection of a steroid such as hydrocortisone into the tendon sheath. This will cure all but the most recalcitrant cases which will need surgery, which consists of laying open the inflamed section of the tendon sheath.

Current treatment/management of trigger finger and DeQuervain's disease appear to suffer from similar disadvantages to those suffered by current treatments for bursitis.

Thus, there is a need for new, improved methods for treating conditions associated with swelling or oedema of body parts/regions, and materials therefor, which overcome one or more of these disadvantages.

SUMMARY OF THE INVENTION

The present investigations have now shown that bursitis, and other conditions resulting in swollen or oedematous body parts/regions or excess body fluid accumulation in body parts or regions can be easily, quickly and economically treated, non-invasively, with compositions which comprise an adsorbent or absorbent agent, and which adsorb or absorb fluids from the body part or region, or the environs thereof. Sanitary napkins, disposable nappies/diapers and sweat patches, as are known in the art and which comprise predominantly a macrofibrous wad or pad, optionally also including polyacrylamide for increased moisture holding capacity are not appropriate for this purpose, as they are not capable of transdermally attracting fluids from the body part or region.

Thus, according to an aspect of the invention, there is provided a method for treating a subject for a condition or inflammation associated with oedema, excess body fluids, or oedema and excess body fluids, or for treating a subject for an abscess, boil, blister or cyst, which method comprises applying to the skin surface covering a body part or region affected by said condition, inflammation, abscess, boil, blister or cyst a composition capable of transdermally attracting fluids from the body part or region or its proximity, wherein said composition comprises at least one adsorptive or absorptive agent, and leaving said composition in contact with the skin for sufficient time to allow said composition to transdermally absorb or adsorb at least a portion of the body fluids from said body part or region.

According to an embodiment, the condition or inflammation is selected from bursitis, trigger finger or DeQuervain's disease.

According to another embodiment, the method is for treating an abscess, boil, blister or cyst.

The composition may be applied to the skin surface covering said body part or region for a time period of from about 4 hours to about 240 hours, optionally replacing said composition with fresh composition once or more during said time period, and in an embodiment the composition is applied once or more nightly (overnight), optionally also applying composition to the body part or region one or more times during the day, replacing the composition or a patch comprising said composition one or more times.

The at least one adsorptive or absorptive agent may be a natural or modified insoluble polymeric substance, and may be selected from natural, modified or synthetic starches, celluloses, dextrin or chitosan, or a polyacrylate or polyacrylamide, or any combination thereof.

The composition may also comprise additional agents, such as at least one warming agent, to increase blood flow to the swollen or oedematous body part/region, one or more weak organic acids, and one or more carriers, excipients, preservatives or additional active agents. Additional active agents may be selected from, for example, anti-inflammatory agents and antimicrobial agents, or combinations thereof.

According to a specific aspect, the present invention provides a method for treating a subject for a condition or inflammation associated with oedema, excess body fluids or oedema and excess body fluids, wherein said method comprises applying to the skin surface covering a body part or region affected by said condition, inflammation, abscess, boil, blister or cyst a composition capable of transdermally attracting fluids from the body part or region or its proximity, said composition comprising:

from about 2% w/w to about 99% w/w of at least one adsorbent or absorbent agent;

from about 0.1% to about 50% of at least one warming agent; and optionally one or more acceptable carriers or excipients or additional active agents.

According to an embodiment, the composition comprises: from about 2% w/w to about 50% w/w dextrin, optionally combined with dehydrated polyacrylamide;

from about 5% to about 40% of crushed tourmaline, amethyst, or a combination of tourmaline and amethyst; and from about 0.1% w/w to about 20% w/w chitosan;

from about 3% w/w to about 50% w/w weak organic acids; optionally one or more acceptable ingredients selected from carriers, excipients, indicators/dyes, preservatives or additional active agents.

According to an embodiment, the composition is contained in a patch adapted for placement onto the body part or region to be treated.

The present invention also provides compositions suitable for use in methods of the invention.

Transdermally absorbing/adsorbing patches for absorbing/adsorbing toxins from the body, particularly through the base of the feet are known. However, these compositions comprise as a significant component wood vinegar and/or bamboo vinegar. Whilst such patches may be used in methods of the present invention, they do suffer the drawback of resulting in body odours subsequent to treatment with these patches. Such patches with high concentrations of these vinegars (up to about 50% total wood/bamboo vinegar) are also known to cause skin irritation. Thus, the present invention seeks to provide an adsorbent/absorbent patch without such drawbacks.

Thus, according to another aspect of the invention, there is provided a composition for absorbing or adsorbing fluids from a body part or region of a subject, wherein said composition is capable of transdermally attracting fluids from the body part or region or its proximity, and wherein said composition comprises at least one adsorptive or absorptive agent, and wherein said composition does not comprise a wood or bamboo vinegar. The composition may comprise components as already described above in the context of methods of the invention.

According to another aspect of the invention, there is provided a composition as described above or a patch comprising such a composition, and which is adapted for placement onto the skin surface covering said swollen or oedematous region.

A patch according to the invention may be for treatment of elbow, shoulder, knee, hip, wrist or foot bursitis, or for treatment of DeQuervain's disease or trigger finger, the patch being specifically adapted for placement on, respectively, the elbow, shoulder, knee, hip, wrist, foot or around or in the proximity of the thumb or fingers.

DETAILED DESCRIPTION OF THE PREFERRED EMBODIMENT

Definitions

As used herein, the term "comprising" means "including principally, but not necessarily solely". Variations of the word "comprising", such as "comprise" and "comprises", have correspondingly similar meanings.

As used herein, the term 'composition capable of transdermally attracting fluids from the body part or region or its proximity' means that the composition actively attracts fluids through the skin, and does not simply passively absorb/adsorb body fluids which are naturally secreted, excreted or perspired from the body, and therefore does not include within its scope sanitary napkins, disposable nappies/diapers, sweat patches or the like.

A "therapeutically effective amount", as referred to herein, includes a sufficient, but non-toxic amount of a compound or composition of the invention to provide the desired therapeutic effect. The "effective amount" will vary from subject to subject depending on one or more of a number of factors amongst, for example, the particular agent being administered, the severity of the condition being treated, the species being treated, the age and general condition of the subject and the mode of administration. For any given case, an appropriate "effective amount" may be determined by one of ordinary skill in the art using only routine experimentation. Typically, "therapeutically effective amount" refers to an amount sufficient to result in one or more or the following: recession/reduction in the extent of the disease, inhibition of disease growth or progression, cessation of disease growth, relief of disease-imposed discomfort, or prolongation of life of the vertebrate having the disease.

As used herein the term "treatment", refers to any and all uses which remedy a disease state or symptoms, or otherwise hinder, retard, or reverse the progression of disease or other undesirable symptoms in any way whatsoever.

As used herein, the term "warming agent" means any agent capable of increasing flow of blood and/or other body fluids to/from the site to which said agent is applied. Such agents may be agents which provide or emit infra-red radiation, agents which cause irritation to a site to which it is applied, or agents which otherwise result in increased blood flow to the site of application of said agent. Such agents may include tourmaline, amethyst, capsaicin, cantharidin, ginsenosides and other natural, or synthetic nitric oxide donors.

DETAILED DESCRIPTION OF THE INVENTION

The present invention is based on the discovery that accumulation of excess body fluids in body parts or regions of subjects, arising from conditions such as bursitis, trigger finger or DeQuervain's disease, can be treated effectively, relatively quickly and economically by applying to the swollen or oedematous body part or region a composition capable of transdermally attracting fluids from the body part or region or its proximity and comprising at least one adsorptive or absorptive agent. Similarly, it is envisaged that abscesses, boils, blisters and cysts, also characterised by subcutaneous fluid retention/formation will also be treatable using methods and compositions capable of transdermally attracting fluids from the body part or region or its proximity and comprising at least one adsorptive or absorptive agent. The present invention also provides compositions for these purposes, but which do not comprise wood vinegar and/or bamboo vinegar.

The at least one adsorptive or absorptive agent may be selected from any appropriate hydrophilic agent including, but not limited to, natural or synthetic fibers, polymers, sugars, organic acids, amino acids, salts, clays, zeolites and other molecular sieves. Thus, according to an embodiment the at least one adsorptive or absorptive agent is selected from: natural or modified polysaccharides; other natural or synthetic insoluble hydrophilic polymers; gel-forming agents; pre-formed, dehydrated gels; silicas; zeolites; molecular sieves; clays; hyperosmotic solids, semi-solids, gels or liquids, or any combination thereof.

Particularly advantageous are polymeric materials, which may be optionally cross-linked, which are typically insoluble, yet hydrophilic, such as natural, modified or synthetic polymeric carbohydrates, including starches, alginates, dextrins, agars, celluloses, chitosan, hemicelluloses, and carboxymethyl, hydroxyethyl and hydroxypropyl derivatives thereof, collagens, polyurethane foams, polyisocyanurate foams, polyacrylates and polyacrylamides, polyvinyl alcohols, polyvinylpyrrolidine, polyethyleneglycol, polylactides(PLA), polyglycolides(PGA), poly(lactide-Co-glycolides), polycarbonate, poly(N-isopropylacrylamide), co-polymer formulations of polymethacrylic acid and polyethylene glycol, co-Polymer formulations of polyacrylic acid and poly(N-isopropylacrylamide), hydrogels, e.g. polyacrylamides, poly(propylene)oxides, pluronic polyol family of gel materials, e.g. pluronic-chitosan hydrogels and silica gels. According to an embodiment, the at least one adsorptive or absorptive agent is a natural or modified starch, cellulose, dextrin or chitosan, or a polyacrylate or polyacrylamide, or any combination thereof.

The at least one adsorptive or absorptive agent may comprise any suitable proportion of the composition. For example, the composition may comprise from about 5% w/w to about 100% w/w of the composition, such as from about 10% w/w to about 90% w/w, from about 10% w/w to about 80% w/w of the composition, from about 15% w/w to about 70% w/w of the composition, from about 15% w/w to about 60% w/w of the composition, from about 15% w/w to about 50% w/w of the composition, from about 15% w/w to about 40% w/w of the composition, from about 20% w/w to about 40% w/w of the composition, from about 20% w/w to about 30% w/w of the composition, about 10% w/w, about 15% w/w, about 20% w/w, about 25% w/w, about 30% w/w, about 35% w/w, about 40% w/w, about 50% w/w, about 60% w/w, about 70% w/w, or about 80% w/w of the composition.

The composition may also comprise at least one warming agent, to improve flow of blood and other body fluids through or past the treated body part/region. Such agents may be agents which provide or emit infra-red radiation, agents which cause irritation to a site to which it is applied, or agents which otherwise result in increased blood flow to the site of application of said agent. Such agents may include tourmaline, amethyst, jade, and certain ceramics which are reputed to emit far infra-red radiation, natural irritants such as capsaicin (the irritant alkaloid of chilies and cayenne pepper) or compositions comprising it and cantharidin (the active agent of Spanish Fly) or compositions comprising it, synthetic irritants, ginsenosides and other natural, or synthetic nitric oxide donors.

Suitable synthetic nitric oxide donors include, for example, nitroglycerine, sodium nitroprusside (SNP), S-nitroso-L-glutathione (GSNO), GSNO monoethyl ester, S-nitroso-N-acetylpenicillamine (SNAP), glyco-SNAP, L-arginine, N,N'-dinitroso-N,N'-dimethylphenylenediamine (BNN3), N,N'-dinitrosophenylenediamine-N,N'-diacetic acid (BNN5), BNN5-Na, BNN5 methyl ester, 2-hydroxybenzoic acid 3-nitrooxymethylphenyl ester (B-NOD), dephostatin, 3,4-dephostatin, diethylamine NONOate, diethylamine NONOate/AM, S,S'-dinitrosodithiol, S-nitrosocaptopril, NG-hydroxy-L-arginine monoacetate salt, Angeli's salt, 1-hydroxy-2-oxo-3-(3-aminopropyl)-3-isopropyl-1-triazene (NOC-5), 1-hydroxy-2-oxo-3-(N-3-methyl-aminopropyl)-3-methyl-1-triazene (NOC-7), 6-(2-hydroxy-1-methyl-2-nitrisohydrazino)-N-methyl-1-hyxanamine (NOC-9), 1-hydroxy-2-oxo-3-(N-ethyl-2-aminoethyl)-3-ethyl-1-triazene (NOC-12), 2,2'-(hydroxynitrosohydrazono)bis-ethanamine (NOC-18), (±)-(E)-Methyl-2-[(E)-hydroxyimino]-5-nitro-6-methoxy-3-hexeneamide (NOR-1), (±)-(E)-4-ethyl-2-[(E)-hydroxyimino]-5-nitro-3-hexeneamide (NOR-3), (±)-N-[(E)-4-ethyl-2-[(Z)-hydroxyimino]-5-nitro-3-hexene-1-yl]-3-pyridine carboxamide (NOR-4), 4-phenyl-3-furoxancarbonitrile, PROLI/NO (L-proline in methanolic sodium methoxide), 3-morphorlinosydnonimine (SIN-1), S-nitroso-N-valerylpenicillamine (SNVP), spermine NONOate, ethyl nitrite and streptozotocin.

In general, nitric oxide donors, including S-nitroso, O-nitroso, C-nitroso and N-nitroso compounds and nitro derivatives thereof and metal NO complexes, but not excluding other NO generating compounds, useful for the purposes of the present invention may be found in "Methods in Nitric Oxide Research," edited by Feelisch, M., and Stamler, J. S., John Wiley & Sons, New York, 1996, pages 71-115, the disclosure of which is incorporated herein by reference. A range of additional nitric oxide donors are known to those skilled in the art and the present invention is not limited by the identity of the particular donor(s) used.

In general, warming agents acting through a chemical mode of action, such as irritants and nitric oxide donors are typically used at low, non-toxic proportions, which will depend on the nature of the warming agent. For example, pure capsaicin would be effective at significantly lower levels than cayenne pepper, and cantharidins may be toxic at even very low levels. The concentration of chemical acting warming agent used may vary from about 0.0001% w/w to about 20% w/w. In particular embodiments, the concentration may be from about 0.001% w/w to about 15% w/w, from about 0.01% w/w to about 10% w/w, from about 0.1% w/w to about 5% w/w, from about 0.5% w/w to about 5% w/w, from about 1% w/w to about 3% w/w, from about 0.001% w/w to about 10% w/w, from about 0.001% w/w to about 5% w/w, from about 0.001% w/w to about 3% w/w, from about 0.001% w/w to about 2% w/w, from about 0.01% w/w to about 1% w/w, from about 0.1% w/w to about 0.5% w/w. Where the warming agent is selected from infra-red emitting minerals, such as tourmaline, amethyst or a combination of both the composition may comprise from about 1% w/w to about 50% w/w, such as from about 5% w/w to about 40% w/w, from about 10% w/w to about 35% w/w, from about 15% w/w to about 30% w/w, from about 20% w/w to about 30% w/w, about 10% w/w, about 20% w/w, about 25% w/w or about 30% w/w warming agent. The most suitable concentration to achieve the desired effect may be determined by those skilled in the art by reference to known literature and using routine experimentation.

The composition may comprise combinations of warming agents acting through different modes of actions, such as combinations of warming agents acting through a chemical mode of action and infra-red emitting agents.

The composition may also comprise one or more additional components selected from preservatives, antioxidants, weak organic acids, carriers, excipients, indicator dyes or additional active agents.

A wide range of appropriate preservatives for use in compositions for use according to the invention, and appropriate dosing levels are well known in the art. Suitable preservatives for use in compositions for use according to the invention include chitosan, triclosan, quaternary ammonium surfactants, thimerosal, benzoic acid or derivatives or salts thereof, parabens, benzylalkonium chloride or salts thereof, volatile oils, including eucalyptus (which has the added benefit of having anti-inflammatory properties) and terpenoids, and weak acids such as sorbic acid or propionic acid, or salts thereof.

Weak organic acids may also improve or enhance absorption of fluids from an affected area. Suitable weak organic acids include, but are not limited to, beta hydroxy acids (BHA) and alpha-hydroxy (fruit) acids (AHA) such as; malic acid, lactic acid, tartaric acid, citric acid or glycolic acid. Without wishing to be bound by theory, organic acids may affect the stability of the connective tissue (such as collagen) underlying the skin and hence may allow additional exchange (release) of body fluids into the patch. Bamboo vinegars, wood vinegars, or both, may also be used in compositions for use in methods according to the invention, but suffer from the drawback of resulting in unpleasant body odours emanating from treated individuals and possible skin irritation if high levels of one or both of these vinegars are used in the composition (such as up to 50% w/w of the composition). These vinegars are also a complex, undefined mixture of components, one or more of which may be toxic, allergenic or otherwise undesirable.

Indicator dyes enable the treated subject to determine whether the composition is exhausted (that is, that the composition is no longer able to adsorb or absorb fluids, or is approaching that limit). Moisture indicators are known based on pH indicators which, depending on the pH value, show a change in color when saturated with bodily fluids and indicate saturation. In addition, moisture indicators based on water-soluble inks are known and described, for example, in EP 0 211 524 B1. Examples of suitable indicators include FD&C No. 1 Blue, and pH indicators such as bromocresol green and bromophenol blue. Such moisture indicators dissolve and disperse on contact with bodily fluids. The dyestuff may be dissolved, suspended or dispersed in the composition. The nature of the colouring agent is unimportant and a wide variety of suitable dyes and pigments will be known to the skilled person. The colouring agent may be soluble or insoluble in water. Generally, however, the dyestuff will be biodegradable so as to fade and not permanently mark the skin or hair.

Examples of other active agents which may be included in the compositions of the invention include anti-inflammatory agents and anti-microbial agents. Anti-microbial agents which are skin permeable, or which are combined with a skin permeation enhancement agent may be of benefit in the treatment of abscesses, boils, blisters, cysts or other swollen/irritated subcutaneous skin conditions.

Examples of suitable anti-inflammatory agents include steroidal anti-inflammatory agents and non-steroidal anti-inflammatory agents (NSAIDS) or immunomodulators, which are skin permeable, or which are combined with a skin permeation enhancement agent. For a discussion of use of penetration enhancers in topical formulations see, for example, percutaneous penetration enhancers (E. W. Smith & H. I. Maibach eds. 1995) or Ghosh, T. K. et al. (1993), Pharm. Tech. 17(3):72-98; Ghosh, T. K. et al. (1993), Pharm. Tech. 17(4): 62-89; Ghosh, T. K. et al. (1993), Pharm. Tech. 17(5):68-76). According to an embodiment, the skin permeation enhancement agent does not interfere with the adsorptive/absorptive properties of the compositions of the invention.

Examples of steroidal anti-inflammatory agents include corticosteroids such as alcometasone, amcinafal, amcinafide, betamethasone, betamethasone benzoate, betamethasone valerate, budesonide, chloroprednisone acetate, clocortolone, clocortolone acetate, cortisone acetate, cortivazol, cortodoxone, descinolone acetonide, desonide, desoximetasone, dexamethasone, dexamethasone 21-phosphate, dichlorisone acetate, difluprednate, flucetonide, flucinolone acetonide, flucinonide, flucloronide, flucortolone, fludrocortisone, fludrocortisone acetate, flumethasone, flumethasone pivalate, flunisolide acetate, fluorometholone, fluperolone acetate, fluprednisolone, fluprednisolone valerate, flurandrenolone acetonide, formocortal, haloprednone, hydrocortisone, hydrocortisone 17-valerate, hydrocortisone 17-butyrate, hydrocortisone 21-acetate, hydrocortisone cyclopentylpropionate, medrysone, nivazol, prednisone, meprednisone, methylprednisone, methyl prednisolone, paramethasone acetate, prednisolamate, prednisolone, prednisolone 21-phosphate, prednival, triamcinolone, triamcinolone acetonide, and triamcinolone hexacetonide.

Examples of non-steroidal anti-inflammatory agents include, for example, arylalkanoic acids, 2-arylpropionic acids, N-arylanthranilic acids (fenamic acids), oxicams, salicylates and sulphoanilides, and may be selected from, for example, aceclofenac, acemetacin, alcofenac, allopurinol, aminopyrine, amoxiprin, antipyrine, apazone, aspirin, azapropazone, benorilate, benzindopyrine hydrochloride, benzydamine hydrochloride, bromfenac, carprofen, choline magnesium salicylate, cinchophen, cintazone, clonixeril, clonixin, colchicine, COX-2 inhibitors (such as celecoxib, etoricoxib, lumiracoxib, parecoxib, rofecoxib, and valdecoxib), demecolcine, desoxysulindac, diclofenac, diflumidone sodium, diflunisal, dimefadane, etodolac, faislamine fenamole, fenbufen, fenoprofen, flufenamic acid, flufenisal, flunixin, fluprofen, flurbiprofen, flutiazin, ibufenac, ibuprofen, indomethacin, indoxole, intrazole, ketoprofen, ketorolac, letimide hydrochloride, licofelone, lomoxicam, loxoprofen, magnesium salicylate, meclofenamic acid, mefenamic acid, melcofenamate, meloxicam, metamizole, metazamide, methyl salicylate, mimbane hydrochloride, molinazole neocinchophen, nabumetone, naproxen, naproxol, nexeridine hydrochloride, nimazole, nimesulide, octazamide, oxaprozen, oxyphenbutazone, oxypurinol, paranylene hydrochloride, phenylbutazone, piroxicam, proxazole citrate, pyrazolidine derivatives, salicylamide, salicyclic acid, salsalate (salicyl salicylate), sulfinpyrazone, sulindac, suprofen, tenoxicam, tesicam, tesimide, tiaprofenic acid, tolmetin, triflumidate, tramadol, tolmetintetrydamine, and triethanolamine salicylate.

Other examples of anti-inflammatory agents which may be included in the compositions of the present invention are herbal and/or natural anti-inflammatory agents, and may be selected from, for example, balsam fir, bioflavonoids (also called flavones or flavonoids, and including compounds such as quercetin, epicatechin, eucalyptus oil, pycnogenol, rutin and oligomeric proanthocyanidins) and sources thereof, black currant oil, blueberry, borage oil, *Boswellia serrata* (Indian frankincense), celery seed, celery seed oil, chamomile (including blue chamomile), cobalamin, cucurmin, devil's claw, fish oil, flaxseed oil, garlic, ginger, glucosamine, glucosamine-chondroitin conjugate, green tea, Kakadu plum (*Terminalia ferdinandiana*), omega-3 fatty acids (including alpha-linolenic acid) and sources thereof, omega-9 fatty acids and sources thereof, oregano, polyphenols and sources thereof, primrose oil, turmeric, vitamins C, D and/or E, willow bark, and wintergreen.

Examples of immunomodulators include azathiopurine, mercaptopurine, adalimumab, infliximab, methotrexate and cyclosporine.

The anti-inflammatory agent may be included in the compositions of the invention at dosage concentrations recommended by the supplier, pharmacopoeias and/or other publicly available publications or information known to those of skill in the art.

Examples of suitable anti-microbial agents include anti-bacterial agents, anti-fungal agents, anti-viral agents and anti-parasitic agents, and which are skin permeable, or which are combined with a skin permeation enhancement agent. Suitable anti-microbial agents may include, for example, preservatives as described above, antibiotics, antimicrobial peptides, cations and minerals (such as silver ions), essential oils, grapefruit seed extract, naldixic acid, nitrofurans, quinolones (including fluoroquinolone), and sulfonamides.

Suitable antibiotics include aminoglycosides (eg. amikacin, gentamycin, kanamycin, neomycin, netilmicin, streptomycin, tobramycin, paromomycin), ansamycins (eg. geldanamycin, herbimycin), carbacefems (eg. loracarbef), carbapenems (eg. ertapenem, doripenem, imipenem/cilastatin, meropenem), cephalosporins (including first, second, third and fourth generations. eg. cefadroxil, cefazolin, cefalotin/cefalothin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime), glycopeptides (eg. teicoplanin, vancomycin), macrolides (eg. azithromycin, clarithromycin, dirithromycin, erythromycin, roxithromycin, troleandomycin, telithromycin, spectinomycin), monobactams (eg. aztreonam), penicillins (eg. amoxicillin, ampicillin, azlocillin, carbenicillin, cloxacillin, dicloxacillin, flucloxacillin, mezlocillin, nafcillin, penicillin, piperacillin, ticarcillin), polypeptides (eg. bacitracin, colistin, polymixin B), quinolones (eg. ciprofloxacin, enoxacin, gatifloxacin, levofloxacin, lomefloxacin, moxifloxacin, norfloxacin, ofloxacin, trovafloxacin), sulfonamides (eg. mafenide, prontosil, sulfacetamide, sulfamethizole, sulfanilimide, sulfasalazine, sulfisoxazole, trimethoprim, trimethoprim-sulfamethoxazole(cotrimazole)), tetracyclines (eg. demeclocycline, doxycycline, minocycline, oxytetracycline, tetracycline), arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin, dalfopristin, rifampin/rifampicin and timidazole.

Examples of essential oils with antimicrobial properties include oregano oil, tea tree (*Melaleuca alternifolia*) oil, mint oil, sandalwood oil, clove oil, *Nigella sativa* (Black cumin) oil, onion oil, leleshwa oil, lavender oil, lemon oil, lemon myrtle oil, eucalyptus oil, peppermint oil, cinnamon oil, clove oil, and thyme oil.

The antimicrobial agent may be included in the compositions of the invention at dosage concentrations recommended by the supplier, pharmacopoeias and/or other publicly available publications or information known to those of skill in the art.

Specific examples of compositions for use according to the invention may comprise:
from about 2% w/w to about 99% w/w of at least one adsorbent or absorbent agent;
from about 0.1% to about 40% of at least one warming agent; and
optionally one or more acceptable carriers or excipients or additional active agents.

Even more specific examples of compositions for use according to the invention may comprise:
from about 2% w/w to about 50% w/w dextrin, optionally combined with dehydrated polyacrylamide;
from about 5% to about 40% of crushed tourmaline, amethyst, or a combination of tourmaline and amethyst; and
from about 0.1% w/w to about 20% w/w chitosan;
from about 3% w/w to about 50% w/w weak organic acids;
optionally one or more acceptable ingredients selected from carriers, excipients, indicators/dyes, preservatives or additional active agents.

Compositions for use according to the invention may be applied to a body part or region to be treated in any appropriate form, such as by direct application of the composition to the body part/region as a gel, poultice, jelly, dressing, plaster, powder, patch, putty or paste.

In many embodiments the composition will comprise mostly, if not solely dry components. To treat a body part or region, such compositions, as well as moist or wet (but hyperosmotic) compositions are advantageously applied to the body part or region in a patch, which may have an adhesive surface, or which is fastened to the swollen/oedematous body part/region.

Figure 1:
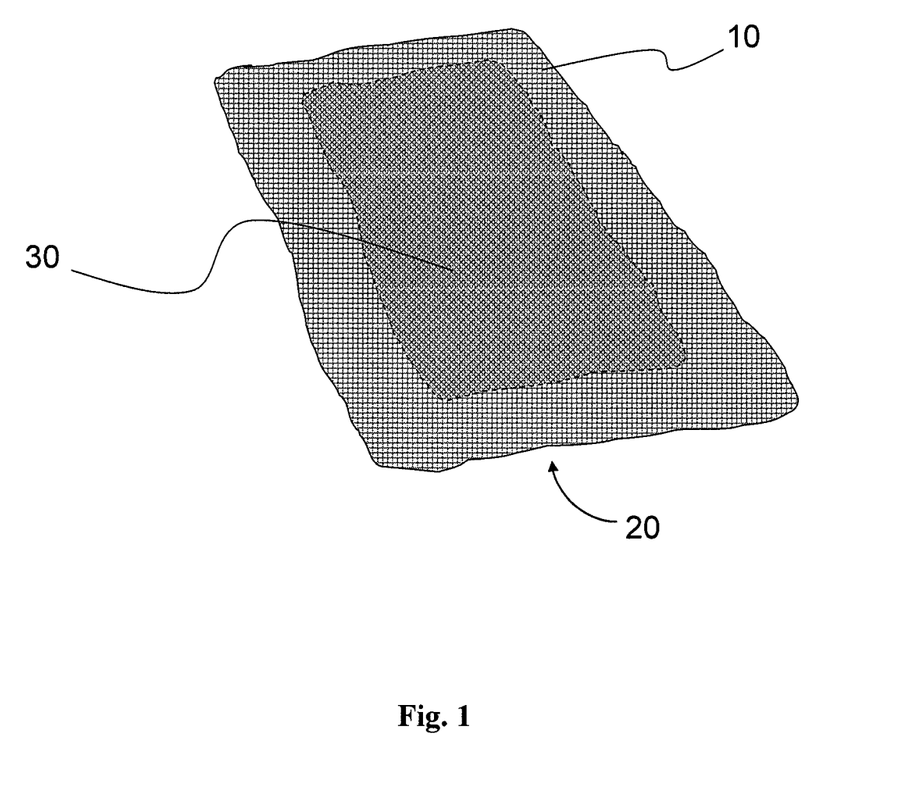
FIG. 1 illustrates a patch comprising a composition according to the invention.

Referring to FIG. 1, a patch according to the invention may comprise a permeable or semi-permeable membrane web 10 which is to come into functional proximity with skin, and a backing web 20 underneath. The two webs are sealed together along their respective perimeters to form composition reservoir 30. Alternatively, one web may be overlapped on all edges by the other web such that the perimeter of one web extends beyond the perimeter of the other when sealed together. In such a configuration, and according to one embodiment, impermeable web 20 is larger in area than membrane 10 such that, when impermeable web 20 and membrane 10 are sealed together to form composition reservoir 30, the perimeter of impermeable web 20 extends beyond the perimeter of membrane 10.

Permeable or semi-permeable membrane 10 is to provide the surface to contact skin and provide diffusional contact between the composition reservoir 30 contents and the skin, and may be constructed of any suitable permeable or semi-permeable material that permits diffusion of fluids across it. Representative permeable or semipermeable materials include, but are not limited to polyethylene, polypropylene, ethylene/vinyl acetate, polyethylene terephthalate, paper, coated paper and other coated or uncoated webs made of natural fibers (such as wood pulp), or natural and synthetic fiber blends, and perforated sheet materials including perforated laminates such as a perforated metallized polyethylene terephthalate/paper laminate. Other suitable materials that can be used along with a water vapor permeable material include impermeable materials such as styrene/butadiene copolymer films.

Backing web 30 defines the side of the matrix patch that, in use, faces the environment (distal to the skin) and which protects external surfaces from fluids which accumulate inside the composition reservoir. The material chosen for the backing should be compatible with the composition inside composition reservoir 30 and with membrane web 10, and should be minimally permeable to any contents of composition reservoir 30. Additionally, the backing web 20 may be made of a sheet or film of a flexible elastomeric material that may be substantially impermeable. The backing web 20 may be of a material that permits the device to follow the contours of the skin, such that it may be worn comfortably on any skin area, e.g., at joints or other points of flexure while minimising the likelihood of the patch disengaging from the skin.

Suitable materials for backing web 20 are well known in the art and include, but are not limited to: polyethylene, polypropylene, polyesters, polyurethanes, polyethylene vinyl acetate, polyvinylidene chloride, block copolymers such as PEBAX, coated webs of natural fibres or natural/synthetic fibre blends, and the like. The backing layer may also comprise laminates of one or more of the foregoing polymers, and may also comprise a thermal isolating material.

Backing web 20 may also comprise one or more moisture indicators which dissolve and disperse on contact with bodily fluids. They can be applied, for example, by printing units, specifically by ink-jet printing. EP 0 211 524 B1 describes the imprinting of an impermeable plastic film as the backing sheet with water-soluble dye, for example in the form of graphics which change under the effects of bodily fluid.

Backing web 20 and membrane web 10 may be sealed together around the periphery by any appropriate means known in the art (e.g., by an adhesive, by heat sealing, or by any other suitable sealing method) with composition according to the invention immobilized within the composition reservoir 30 formed between backing web 20 and membrane web 10.

The edges of the patch on the side of permeable or semipermeable membrane 10 may optionally be coated with an adhesive for keeping the membrane 10 in at least partial contact with the skin once applied. If using an adhesive which does not interfere with fluid communication between composition reservoir 30 and the skin to which it is applied, substantially the whole of the surface of the patch on the side of membrane web 10 may be coated with said adhesive. Alternatively, if the adhesive is hydrophobic and is to cover the surface of the web, it may be applied to the web in a discontinuous manner (such as in a random mesh of fibres, with substantial spaces therebetween) so as to not impede flow of liquids. Suitable adhesives are well known in the art and may include, for example, thermoadhesives and contact adhesives such as cross-linked acrylates.

Instead of using an adhesive surface, the patch may be held in place, with membrane 10 in at least partial contact with the skin, by applying a bandage, which may be adhesive or which wraps around a body part or region.

To maintain the composition inside the web substantially fresh, and to protect it from external moisture before use, one or more complementarily fitting or overlapping peel-away webs which are at least partially fluid impervious, may optionally cover at least the surface of membrane 10 defining composition reservoir 30, although it may be more practical for the peel-away web(s) to cover the full surface of membrane 10 (including the perimeter thereof sealed to backing web 20). The peel-away web(s) may be constructed by any suitable material, for example, but not limited to metal foils, metalized polyfoils, composite foils or films containing polyester such as polyester terephthalate, polyester or aluminized polyester, polytetrafluoroethylene, polyether block amide copolymers, polyethylene methyl methacrylate block copolymers, polyurethanes, polyvinylidene chloride, nylon, silicone elastomers, rubber-based polyisobutylene, styrene, styrene-butadiene, and styrene-isoprene copolymers, polyethylene, and polypropylene, or other suitable films coated with an appropriate release surface. Peel-away web may also, or additionally, protect adhesive on the skin-contacting (membrane 10) side of the patch from the external environment until application of the patch to a skin surface.

An alternative means for protecting the patch and the adsorptive absorptive composition within is to seal the patch in a sachet, or similar, of a suitable barrier material, such as may be made using the same materials as peel-away webs as described above, or other suitable barrier films as are known in the art.

Examples of transdermal patches, and methods for making them, are also described in U.S. Pat. Nos. 5,122,383 and 5,460,820.

A patch comprising a composition for use according to the invention may be specifically adapted for placement onto particular body surfaces. For example, the patch may be for treatment of elbow, shoulder, knee, or hip bursitis, or for treatment of DeQuervain's disease or trigger finger, and be specifically adapted for placement on, respectively, the elbow, shoulder, knee, hip, wrist or around or in the proximity of the thumb or fingers.

The size and shape of the patch will depend on the skin surface covering the body part or region to which it is to be applied. In addition, the patch may comprise extensions of the backing web 20, or of membrane web 10 which act as fastening means (for example, adhesive flaps or straps, or elastomeric bandaging) to aid in holding the patch in place on the body part or region to be treated. Alternatively, such features may be provided by one or more separately attached material webs.

Figure 2:
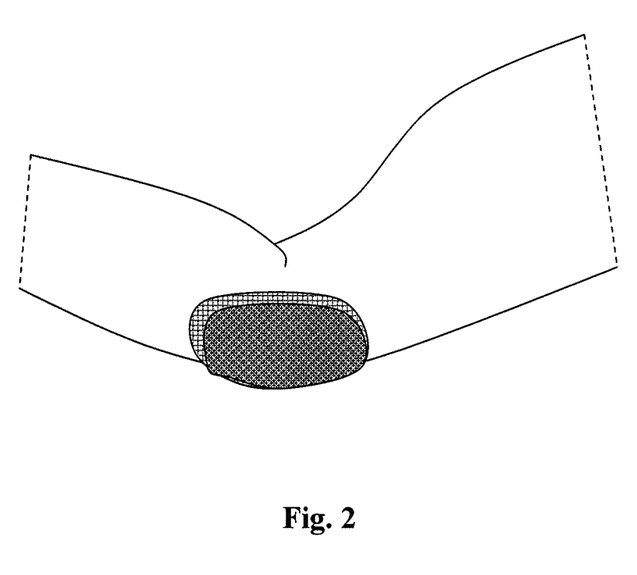
FIG. 2 illustrates a typical placement of a patch comprising a composition according to the invention, for the treatment of elbow (olecranon) bursitis.

For example, having reference to FIG. 2, a patch for treatment of elbow (olecranon) bursitis, may be adapted for placement on the outer/posterior bend of a swollen elbow. Such a patch may have a membrane 10 surface defining the membrane side of composition reservoir 30 (operative area) having an area of from about 25 to about 200 $cm^2$. Patches for application to the knee area would generally be of a similar size, those for application to the heel, foot or wrist may typically be slightly smaller, having an operative area of from about 25 to about 150 $cm^2$, those for application to a finger may be smaller again, having an operative area of from about 10 to about 80 $cm^2$, those for application to the shoulder and hip areas may be significantly larger, and may have an operative area of from about 25 $cm^2$ to about 300 $cm^2$ or 25 $cm^2$ to about 400 $cm^2$, respectively. The patch may additionally comprise one or more flanges, flaps or straps of web material, which may be adhesive or elastomeric, for securing, or further securing (if the membrane 10 side of the patch is at least partially coated with adhesive) the patch to the elbow. Where the one or more flanges, flaps or straps of web material comprise non-adhesive material, this may form, with the patch, a slip-on device which girdles the elbow, holding the patch against the outer/posterior bend of the elbow.

Corresponding configurations may be designed for patches of the invention intended for treatment of other forms of bursitis, such as hip bursitis, shoulder bursitis or prepatellar bursitis, or trigger finger or DeQuervains's disease.

Methods for treating body parts or regions for bursitis, trigger finger, DeQuervain's disease, boils, blisters or cysts, or other condition associated with oedema and/or accumulation of excess body fluids in a body part or region may comprise applying to the skin surface covering said body part or region a composition or a patch according to the invention as described above. The composition or patch may be kept in contact with the skin covering the affected body part or region for sufficient time to allow the composition to absorb or adsorb at least a portion of the fluids associated with the condition. Suitable time periods for achieving the desired result may vary significantly, depending on the condition being treated and the extent thereof, as well as on the amount of composition or size of patch applied, and may range from about 6 hours (such as overnight) to about 30 days or more (particularly where a composition or patch is applied at night only).

The composition or patch may be replaced one or more times during the treatment period, as may be required once the absorbent/adsorbent properties of the composition become exhausted. Determination of whether the adsorbent/absorbent properties of the composition have been exhausted may be assisted by the presence of a moisture indicator, such as a moisture indicator dye as described above.

Alternatively, compositions or patches according to the invention may be applied nightly, for approximately 6-8 hours each night, applying fresh composition or patches each night, until the desired results are achieved. Patches may also be applied one or more times during the day as well, optionally replacing the patch with a fresh patch one or more times.

Without wishing to be bound by theory, it is believed that the compositions of the invention work by promoting movement of body fluids from the affected area into the patch. Alternatively, the compositions may absorb normal fluids from the tissue surrounding the affected area, which then causes an osmotic effect that induces the inflammatory fluids out of the affected area and into the surrounding tissue. Where the composition also comprises a warming agent, it is believed that the composition works by promoting additional removal of fluids via inducing perspiration; promoting healing via warming the injured area and increasing blood flow, or by both of these mechanisms. If the composition does not comprise a warming agent, at least the treated body part region may be heated using external means, or may be treated with a warming agent before or during treatment with a composition according to the invention. The composition or patch may also be heated before application to the body part/region to be treated. Alternatively, if desired, the composition patch may be cooled before application to a body part or region to be treated, although this may slow transfer of fluids from the treated area into the composition. Where the composition or patch is to be warmed or cooled, the composition or patch may comprise a hyperosmotic gel, or other adsorptive/absorptive formulation having a relatively high thermal inertia compared to dried powders/fibrous material.

Conditions which may be treated or at least of which symptoms may be alleviated, may include any condition that results in accumulation of fluids in a body part or region. Such conditions may, for example, include various forms of bursitis, such as elbow bursitis (olecranon bursitis), shoulder bursitis, trochanteric (hip) bursitis and prepatellar (kneecap) bursitis, and bursitis in the region of the Achille's tendon, the foot and the wrist. Other conditions that may be treated by methods of the invention may include, for example, stenosing tenosynovitis (trigger finger) and DeQuervain's Syndrome, as well as arthritis, tendonitis or sports injuries. Yet further conditions which may be treated by methods of the invention, or using compositions of the invention include abscesses, boils, blisters and cysts. Methods and compositions according to the present invention may also be beneficial in treating post operative edema or lung and heart conditions that result in fluid retention, on or in lung(s) such as pleurisy, pneumonia, congestive heart failure or post operation.

Where abscesses, boils, blisters (which may become infected) or cysts are to be treated, compositions used for their treatment may comprise an antimicrobial agent as described above. In this manner, while reducing pressure due to fluids in the boil/blister/cyst, the antimicrobial agent may treat the infection.

Preferred forms of the present invention will now be described, by way of example only, with reference to the following examples, including comparative data, and which are not to be taken to be limiting to the scope or spirit of the invention in any way.

Example 1

Materials and Methods

Patches comprising the following composition are applied to the affected area at least nightly:
Wood Vinegar 5% w/w
Tourmaline 1% w/w
Chitosan 3% w/w
Pearl Stone 7% w/w
Highly purified silica 5% w/w
Polyolic alcohol 5% w/w
Starch 73% w/w
Mugwort extract 1% w/w The composition is packaged into a patch comprising a membrane web and a backing web, each being approximately 90 mm in length and approximately 60 mm in width, heat-pressed together along their perimeters and thereby defining a reservoir in which the composition was located. Both the membrane web and the backing web comprise a layer of cellulose-based fibres treated with a thermoadhesive layer. The cellulose-based layer of the membrane web is non-woven, perforated and textured, and the thermoadhesive layer thereof is discontinuous, being composed of a mesh of randomly aligned adhesive fibres. The cellulose-based layer of the backing web is non-woven and continuous, and the thermoadhesive layer is continuous, thereby also acting as an impermeabilising layer. The thermoadhesive layers of the membrane and backing webs are arranged such that they face each other (for heat welding the two webs together).

The patches are applied to the desired area using a resilient/flexible and elastic fibre-reinforced pressure-sensitive adhesive web.

Example 2

Results

Individual 1

Bursitis presented on the elbow (olecranon bursitis) as a swollen region approximately 2.5-5 cm in diameter and about 0.5 cm high. The pain level was moderate to high, suffered for less than 1 month.

The bursitis had completely healed after 1 overnight patch application.

Individual 2

Acute elbow (olecranon) bursitis presented overnight as a result of impact to the elbow region. The resulting swollen region was more than 5 cm in diameter and more than 2.5 cm high but no pain was associated.

After a first overnight application of a patch to the affected region, the next morning the swelling was reduced somewhat. After a subsequent overnight patch application, the elbow swelling was reduced at least 30%. After a third overnight patch application, the swelling was so reduced that it the bursa was only slightly stretched out and, after a fourth overnight patch application the swelling had effectively disappeared.

Individual 3

Bursitis with a swollen region approximately 2.5-5 cm in diameter presented on the knee over long term (1-3 months) with moderate associated pain.

The pain was gone after the third overnight patch application. The swelling was almost completely gone after 6-9 patch applications.

Individual 4

Chronic bursitis with a swollen region approximately 2.5-5 cm in diameter presented on the foot, on the lateral side next to the small toe for more than 12 months. Associated pain varied with type of footwear worn, with pain levels ranging from insignificant to strong. The individual's orthopedic surgeon had recommended surgery to remove the bursa and shave the bone.

Patches were applied overnight over three weeks (each patch re-used over seven nights: three patches in total). Although the patches did not totally remove the swelling (possibly due to incorrectly re-using each patch over several days, instead of using fresh patches for each application), it was greatly reduced and associated pain had all but disappeared, and surgery now appears unnecessary.

Individual 5

Bursitis with a swollen region of more than 5 cm in diameter and 1.5-2.5 cm height presented on the knee over long term (1-3 months) with moderate to strong associated pain. The swollen area had developed a bad infection, and therefore antibiotics were taken to clear the infection before trial of the patches.

After four overnight patch applications, the swelling had been reduced significantly and the pain had gone. This individual then ran out of patches, but the swelling was still subsiding slowly.

Individual 6

Chronic bursitis presented on the left shoulder for 3 years. Prior to using the patches the only relief was via cortisone shots, directly in the bursa sac. The individual could not lift their arm over their head at all.

On initial application of a patch to the swollen area, a relaxed feeling spread to the area within 15 minutes, and the individual's prescribed anti-inflammatories and pain killers were not required. After three overnight patch applications the pain had totally subsided, and cortisone injections were no longer required (up to three months after the treatment).

It will be appreciated that, although specific embodiments of the invention have been described herein for the purpose of illustration, various modifications may be made without deviating from the spirit and scope of the invention as defined in the following claims.

What is claimed is:

1. A method for treating a subject for a bursitis, which method comprises applying to the skin surface covering a body part or region affected by said bursitis a composition consisting essentially of a dry adsorptive or absorptive agent, a warming agent, and optionally:
    (i) one or more weak organic acids;
    (ii) one or more preservatives;
    (iii) one or more indicator dyes;
    (iv) one or more carriers;
    (v) one or more excipients; or
    (vi) any combination of (i) to (v);
said composition being in diffusional contact with the skin, and leaving said composition in contact with the skin for sufficient time to allow said composition to adsorb or absorb fluids from the skin to treat said bursitis,
    wherein said warming agent is tourmaline, amethyst, jade, and a far infra-red emitting ceramic, or any combination thereof,
    wherein said warming agent is not a nitric oxide donor, and
    wherein said dry adsorptive or absorptive agent is not macrofibrous.

2. A method according to claim 1, wherein said composition is applied to said skin surface for a time period of from about 4 hours to about 240 hours, optionally replacing said composition with fresh composition once or more during said time period.

3. A method according to claim 1, wherein said composition is applied at night.

4. A method according to claim 3, wherein said composition is also applied one or more times during the day, optionally replacing the composition one or more times.

5. A method according to claim 1, wherein said adsorptive or absorptive agent is a natural polysaccharide; a modified polysaccharide; a natural insoluble hydrophilic polymer; a synthetic insoluble hydrophilic polymer; a gel-forming agent; a pre-formed, dehydrated gel; a silica; a zeolite; a molecular sieve; a clay; a hyperosmotic solid or any combination thereof.

6. A method according to claim 1, wherein said at least one adsorptive or absorptive agent is a natural starch, a modified starch, dextrin, chitosan, a polyacrylate a polyacrylamide or any combination thereof.

7. A method according to claim 1, wherein said warming agent is crushed tourmaline, crushed amethyst, or a combination thereof.

8. A method according to claim 1, wherein said composition consists essentially of a dry adsorptive or absorptive agent, a warming agent, one or more weak organic acids, and optionally:
    (i) one or more preservatives;
    (ii) one or more indicator dyes;
    (iii) one or more carriers; or
    (iv) one or more excipients; or
    (v) any combination of (i) to (v);
    wherein said warming agent is tourmaline, amethyst, jade, a far infra-red emitting ceramic, or any combination thereof.

9. A method for treating a subject for a bursitis, wherein said method comprises applying to the skin surface covering a body part or region affected by said bursitis a composition consisting essentially of:
    from about 2% w/w to about 99% w/w of a dry adsorbent or absorbent agent;
    from about 0.1% to about 50% of a warming agent, optionally one or more acceptable carriers or excipients;

wherein said warming agent is tourmaline, amethyst, jade, a far infra-red emitting ceramic, or any combination thereof, wherein said warming agent is not a nitric oxide donor, wherein said dry adsorptive or absorptive agent is not macrofibrous and is in diffusional contact with the skin, and wherein said composition is left in contact with the skin for sufficient time to adsorb or absorb fluids from the skin to treat said bursitis.

10. A method according to claim 9, wherein said composition consists essentially of:

from about 2% w/w to about 50% w/w dextrin, optionally combined with dehydrated polyacrylamide;

from about 5% to about 40% of crushed tourmaline, amethyst, or a combination of tourmaline and amethyst; and from about 0.1% w/w to about 20% w/w chitosan;

from about 3% w/w to about 50% w/w weak organic acids;

optionally one or more acceptable ingredients selected from carriers, excipients, indicators/dyes and preservatives.

11. A method according to claim 1, wherein said composition is contained in a patch adapted for placement onto said skin surface.

12. A method according to claim 1, wherein said composition consists essentially of a dry adsorptive or absorptive agent, a warming agent, at least one antimicrobial agent as a preservative and optionally:

(i) one or more weak organic acids;
(ii) one or more indicator dyes;
(iii) one or more carriers; or
(iv) one or more excipients; or
(v) any combination of (i) to (v);

wherein said warming agent is tourmaline, amethyst, jade, a far infra-red emitting ceramic, or any combination thereof.

13. A method according to claim 1, wherein said adsorptive or absorptive agent is combined with said warming agent.

* * * * *